United States Patent [19]

Simonidesz et al.

[11] Patent Number: 4,520,018

[45] Date of Patent: May 28, 1985

[54] 5-SUBSTITUTED-4-OXO-PGI$_1$ DERIVATIVES, PGI$_1$ COMPOUNDS OF SIMILAR STRUCTURE, THEIR PHARMACEUTICAL METHODS AND PROCESS FOR THE PREPARATION OF SAID COMPOUNDS

[75] Inventors: Vilmos Simonidesz; József Ivanics; Géza Galambos; Ágnes Papp neé Behr; Gábor Kovacs; Judit Skopál; Ildikó Szilágyi, all of Budapest, Hungary

[73] Assignee: Chinoin Gyogyszer es Vegyeszeti Termekek Gyara Rt., Budapest, Hungary

[21] Appl. No.: 369,543

[22] Filed: Apr. 19, 1982

[30] Foreign Application Priority Data

Apr. 14, 1981 [HU] Hungary ................................ 965

[51] Int. Cl.$^3$ ................ A61K 31/557; A61K 31/335; C07D 307/935

[52] U.S. Cl. .................................. 514/469; 549/214; 549/465; 514/470

[58] Field of Search .............. 549/465, 214; 542/423, 542/426, 429; 424/184, 285

[56] References Cited

U.S. PATENT DOCUMENTS

| | | | |
|---|---|---|---|
| 4,126,744 | 11/1978 | Ayer | 549/465 |
| 4,330,553 | 5/1982 | Simonidesz et al. | 549/465 |
| 4,430,497 | 2/1984 | Vollenberg et al. | 549/465 |
| 4,438,132 | 3/1984 | Gatambos et al. | 549/465 |

*Primary Examiner*—Henry R. Jiles
*Assistant Examiner*—Bernard I. Dentz
*Attorney, Agent, or Firm*—Karl F. Ross; Herbert Dubno

[57] ABSTRACT

New PGI$_1$ derivatives are disclosed as well as a process for the preparation thereof, pharmaceutical compositions containing same and methods of treatment employing same. The new compounds are useful to inhibit blood platelet aggregation induced by ADF, arachidic acid, or collagen, as well as to improve blood circulation and to inhibit gastric acid secretion.

56 Claims, No Drawings

5-SUBSTITUTED-4-OXO-PGI₁ DERIVATIVES, PGI₁ COMPOUNDS OF SIMILAR STRUCTURE, THEIR PHARMACEUTICAL METHODS AND PROCESS FOR THE PREPARATION OF SAID COMPOUNDS

The present invention relates to new, biologically active 5-substituted PGI$_1$ derivatives of formula (I)

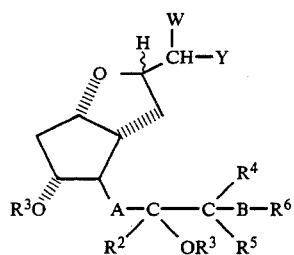

and to a process for the preparation thereof. Both optically active and racemic forms of the novel compounds as well as salts thereof formed with pharmacologically acceptable cations are within the scope of the invention.

The substituents in formula (I) have the following meanings:

W is —COOR$^1$, —CN or —NO$_2$, alkanoyl of from one to four carbon atoms, alkylsulfenyl of from one to four carbon atoms, arylsulfenyl, substituted arylsulfenyl, alkylsulfonyl of from one to four carbon atoms, arylsulfonyl, substituted arylsulfonyl, or arylselenyl, in general an electrophilic group, R$^1$ is hydrogen, straight or branched alkyl of from one to six carbon atoms, cycloalkyl of from three to ten carbon atoms, aralkyl or aryl, Y is hydrogen (in case W is nitro), —COOR$^1$, —COR$^1$, —CN or

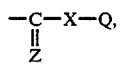

wherein

Z is oxygen, or if W is nitro, Z means two hydrogens,
X is —CH$_2$—CH$_2$—, —CH=CH—, —CH$_2$—C(CH$_3$)$_2$—, —(CH$_3$)$_2$C—CH$_2$—, phenyl—S—CH—CH$_2$—, —CH$_2$—CH—S—phenyl,

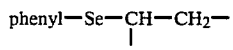

or cyclopropylene,

Q is —COOM, —COOR$^1$, —CH$_2$—OH or —COL$^1$, wherein
M is a pharmacologically acceptable cation,
L$^1$ is —NH$_2$, —NHR$^1$ or —NR$^1$R$^1$,
A is trans—CH=CH—, —C≡C— or —CH$_2$—CH$_2$—,
R$^2$ is hydrogen having a steric position of α- or β-, or methyl or ethyl,
R$^4$ and R$^5$ are independently hydrogen, or alkyl having of from one to four carbon atoms,
R$^3$ is hydrogen, or a protecting group which may be an alkanoyl of from one to four carbon atoms, an unsubstituted or substituted aroyl or a tri—C$_{1-4}$alkylsilyl,
R$^6$ is straight or branched alkyl of from one to six carbon atoms, aryl, substituted aryl or substituted heteroaryl,
B is methylene, oxygen or —NH.

The novel compounds of formula (I) themselves also show pharmacological activity, furthermore they are useful intermediates to the preparation of novel, stable PGI$_2$ analogues, namely 4-oxo-PGI$_1$ and derivatives thereof. The compounds of formula (I) inhibit the blood platelet aggregation induced by ADP, arachidic acid or collagen, furthermore they affect the blood circulation, inhibit the gastric acid secretion, after the gastrointestinal system and show many other valuable pharmacological properties in a concentration of from 1 to 100 γ/ml.

(A) VASODILATING EFFECT

The novel prostacyclin analogues of the invention possess a peripheral vasodilating effect of similar strength as the prostacyclin itself. Therefore they can be used for treatment or prophylaxis of various diseases of the cardiovascular system, like artheriosclerosis obliterans, myocardial infarction, thrombosis, diseases caused by vasoconstriction, and hypertension. The compounds of the invention can be administered in the form of intravenous infusions, intramuscularly or subcutaneously, furthermore orally, in the form of tablets or capsules. The daily dose is about 0.1–100 mg depending upon the age of the person to be treated and the seriousness of the disease. Certain compounds, particularly the 5-nitro-PGI$_1$ and derivatives thereof show high selectivity; in addition to the strong vasodilating effect they exert less intensive other prostacyclin-like effects. Strength of the hemodinamical effect is of the same order of magnitude as that of the PGI$_2$ (the dose equipotent with PGI$_2$ is 0.1–0.5 μg/kg body weight in anaesthetized cats), while the antiaggregatory effect is 1000–10000 times weeker than that of the PGI$_2$. The blood platelet aggregation induced in human blood by 1×10$^{-6}$ mole/ml ADP could be inhibited using certain novel compounds in a concentration of 5–100 μg/ml (IC$_{50}$), measured with the Born-method.

(B) BLOOD PLATELET ANTIAGGREGATORY EFFECT

The novel prostacyclin analogues inhibit the blood platelet aggregation, reduce adhesion of the blood platelets, inhibit the formation of thrombi and have a desaggregatory effect, that is dissolve that thrombi already formed. Thus they are suitable for treatment and prophylaxis of thrombotical processes, for treatment of anginal diseases, during special heart operations to terminate coagulability of blood in the process of extracorporal circulation, and to ensure its optimal parameters. The compounds are administered preferably orally, in the form of tablets or capsules, 2–4 times a day. The daily dose is between 0.05 and 100 mg. The novel compounds in vitro inhibit the blood platelet aggregation induced by arachidic acid, ADP or collagen, in a concentration of 0.01–100 γ/ml.

(C) INHIBITION OF GASTRIC ACID SECRETION

The novel prostacyclin analogues are applicable in the human or veterinary therapy for inhibiting and affecting gastric acid secretion, they reduce or eliminate the possibility of forming ulcers, furthermore promote curing of same. The daily dose is 0.01–10 mg/kg body weight in the form of intravenous or subcutaneous injection or in the form of infusion. The oral daily dose is 1-100 mg.

(D) BRONCHUS DILATATION

The novel prostacyclin analogues are suitable for treatment of asthma as bronchodilatators and inhibitors of the mediator compounds of asthma. They can be administered in the form of tablets, capsules or aerosols, in a dose of 0.01-10 mg/kg body weight/day. They can advantageously be combined with other known antiasthmatics, e.g. with isoproterenol, ephedrine, etc.

Furthermore the novel compounds can be used for treatment of different skin diseases, e.g. psoriasis, different specific and aspecific dermatitises, allergic exanthemas. In this case they are formulated as ointments, solutions or aerosols, with an active ingredient content of 0.5-4%.

According to the invention the compounds of formula (I) are prepared from the bicyclic hemiacetals of formula (II),

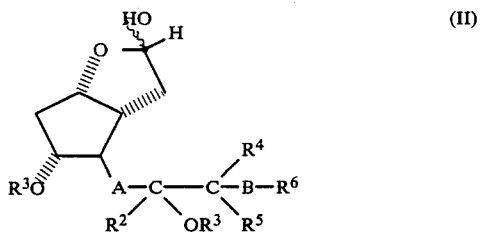

wherein the substituents are as defined in formula (I), by reacting them with the compounds of formula (III)

containing an active methylene group. In formula (III) the substituents are as defined in formula (I).

The above preparation of the compounds of formula (I) is based on the Knoevenagel condensation, which was not applied in the prostacycline chemistry till now. By this reaction starting from the compounds of formula (II) the α-chain of the prostacyclin analogues and the bicyclic product can be manufactured in one step.

In the course of the Knoevenagel reaction interaction of oxo-derivatives and of compounds containing an active methylene group, in general α-dicarbonyl-derivatives, leads to α,β-unsaturated dicarbonyl compounds (Berichte, 1869, 29, 172, and J. Am. Chem. Soc. 1937, 59, 2327).

According to the invention the compounds of formula (II) are applied as molecules containing a hidden aldehyde function, and they are reacted with the compounds of formula (III) in the presence of catalyst(s) used in the Knoevenagel condensation. The α,β-unsaturated dicarbonyl compounds and the bifunctional and nitro derivatives formed in the reaction can not be isolated, since they react immediately with the C-9-hydroxy of the prostaglandin-chain are transformed into the cyclic product of formula (I). The desired compounds of formula (I) are obtained either directly from the reaction mixture or after the acidic or alkaline hydrolysis thereof.

The new, convergent, one-step synthesis not applied yet in the preparation of prostaglandins, in addition to its chemical novelty is significant because it ensures a simple, extraordinarily economic synthesis for manufacturing the compounds of formula (I). Up to now the prostacyclin derivatives of similar structure were prepared from the compounds of formula (II) by Wittig-alkylation, then subjecting the obtained $PGF_{2\alpha}$ to a halocyclization or to an electrophilic addition and then to a cyclization. (J. Am. Chem. Soc., 1977, 99, 2006).

Compounds of formula (II) are known in the literature (J. Am. Chem. Soc., 1969, 91, 5675) or can be prepared by known methods from the corresponding starting materials. Compounds of formula (III) are partly known as β-dicarbonyl compounds or methylene group containing compounds with two active groups (Patai, S.: The Chemistry of the Carbonyl Group, Interscience Publ., London, 1966). Preparation of the novel compounds of formula (III) will be disclosed later in details.

Generally methylene compounds containing two active groups are used in the Knoevenagel reaction. Electrophilic character, carbanion stabilizing ability of the nitro group is enough in itself to carry out the Knoevenagel condensation, therefore if W is nitro in formula (III), the condensation reaction may be carried out even if Z stays for two hydrogen atoms.

According to the invention the compounds of formula (II) wherein $R^3$ is hydrogen or a hydroxy-protecting group defined above, are reacted with the compounds of formula (III) in the presence of a solvent or without solvent [using an excess amount of the compound of formula (III) as a solvent] at a temperature of from 25° to 200° C., in the presence of the catalysts generally used in the Knoevenagel condensation. As a solvent preferably an aromatic hydrocarbon, e.g. benzene toluene or xylene is applied and the reaction is performed at the boiling point of the solvent. Under such circumstances the water liberated in the reaction forms an azeotrope with the solvent and so distills off from the system, shifting the balance of the reaction towards the favoured side. As a solvent, also an other inert compound, e.g. dimethyl formamide, dimethyl sulfoxide, hexamethylphosphoric acid triamide or a chlorinated aliphatic or aromatic hydrocarbon can be used. The applied catalyst may be selected from a group consisting of different bases and acids, and the salts thereof, preferably secondary amines, piperidine, morpholine, dialkyl amines and the salts thereof formed with organic acids, preferably with acetic acid, furthermore organic acids, preferably acetic acid and sulfonic acids, Lewis acids, preferably boron trifluoride etherate, zinc(II)-chloride, titanium(IV)-chloride et., furthermore amino acids.

According to the most advantageous embodiment of the process a benzene or toluene solution of a compound of formula (II) is boiled together with an amount of from 1 to 5 equivalents of a compound of formula (III) in the presence of catalytical or in certain cases equivalent amount of piperidinium acetate or piperidine. The reaction time is 2 to 72 hours depending upon the structure of the compounds of formula (III), and the compounds of formula (I), which are less polar than the compounds of formula (II), are obtained almost quantitatively. Compounds of formula (I) may be isolated by purifying on a chromatographical column, or by crystallization. If desired, compounds of formula (I) may be transformed into another compounds within the scope of formula (I) by alkaline or acidic hydrolysis or by reduction. Alternatively, if desired, compounds of formula (I), wherein $R^3$ is hydrogen, may be transformed into compounds of formula (I), wherein $R^3$ is a hydroxy-protecting group, by reacting former ones with one of the above reagents capable to transfer a hydroxy-protecting group.

A further advantage of the process according to the invention is that those compounds of formula (I), wherein $R^3$ is hydrogen, may be prepared directly from the corresponding compounds of formula (II), wherein $R^3$ is hydrogen, while those compounds of formula (I), wherein $R^3$ is a hydroxy-protecting group, may be prepared directly from the corresponding compounds of formula (II), wherein $R^3$ is a hydroxy-protecting group.

In the specification the term $C_{1-4}$ alkyl is used to designate the following alkyl groups: methyl, ethyl, n-propyl, isopropyl, n-butyl, isobutyl, sec-butyl, tert-butyl. The $C_{1-4}$ alkanoyl groups are the ones which correspond to the $C_{1-4}$ alkyl groups defined above; namely the formyl, acetyl, propionyl and butiryl groups. Term $C_{1-6}$ alkyl covers the different pentyl and hexyl groups in addition to the $C_{1-4}$ alkyl groups enumerated hereinabove. The term aryl in the specification covers the phenyl group. The aryl group may be unsubstituted or substituted by one or more halogen, phenyl, $C_{1-4}$ alkyl, or halo—$C_{1-4}$ alkyl group(s), at any position(s). The aralkyl group may be a $C_{1-4}$ alkyl substituted by an aryl defined hereinabove.

Term $C_{1-4}$ alkylsulfenyl is used to designate those groups in which the $C_{1-4}$ alkyl is attached through a sulfur atom. In the arylsulfenyl groups it is an aryl group which is attached through a sulfur atom. The above groups are also named $C_{1-4}$ alkylthio and arylthio groups, respectively. In the $C_{1-4}$ alkylsulfonyl and arylsulfonyl groups the alkyl and the aryl groups are attached through an —$SO_2$— group. In the arylselenyl group the aryl part is attached through a selenium atom.

The $C_{3-10}$ alkyl group may be e.g. cyclopropyl, cyclopentyl, cyclohexyl, cycloheptyl, cyclooctyl, cyclononyl or cyclodecyl.

In the specification, if not otherwise stated, the term pharmacologically acceptable cation is used to designate one equivalent of a one-, two- or three-valent positive cation, which in an amount corresponding to the doses according to the invention provoke no undesirable side-effects in the living organism. Such cations are first of all the alkali metal ions, e.g. the sodium, potassium and lithium ions, the alkaline earth metal ions, e.g. the calcium, the magnesium, the aluminium and the ammonium ions, and the one-, two- or multi-valent ammonium ions derived from organic amines, e.g. the tris(hydroxymethyl)-ammonium ion.

Alkyl groups of the tri—$C_{1-4}$ alkyl-silyl groups may be identical or different. The heteroaryl group may contain one or more hetero atoms, such as nitrogen, oxygen or sulfur, at any position(s) of the ring.

The following Examples illustrate the invention without restricting its scope.

EXAMPLES

EXAMPLE 1

5-Ethoxycarbonyl-4-oxo-PGI$_1$-ethylester (compound of formula (I), wherein W is ethoxycarbonyl, A is trans-vinyl, Y is a group of formula

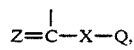

Z is oxygen, X is —$CH_2$—$CH_2$—, Q is ethoxycarbonyl, $R^2$ is hydrogen having a steric position of $\beta$, $R_3$ is hydrogen, $R^4$ and $R^5$ are independently hydrogens, B is methylene, $R^6$ is propyl)

5.8 g (21.5 mmoles) $3\alpha,\beta$-hydroxy-$6\beta$-(3S-hydroxy-oct-1E-enyl)-$7\alpha$-hydroxy-2-oxabicyclo[3.3.0]octane and 9.3 g (43 mmoles) 3-oxo-diethyladipate were dissolved in 60 ml water-free benzene, and 4.3 ml catalyst solution (containing 42.8 g (0.5 moles) piperidine and 60 g (1 mole) acetic acid in benzene up to 1000 ml) was added thereto. The reaction mixture was refluxed for one and a half to two hours on an oil bath, under a Soxhlet extractor or a water separator. The reaction was followed by thin layer chromatography (practically quantitative) then the reaction mixture was diluted with 100 ml ethyl acetate, the organic layer was extracted twice, both times with 20 ml water, then washed with 20 ml of a saturated aqueous sodium chloride solution, dried over anhydrous sodium sulfate, filtered and the solvent was distilled off. The 14 g crude product was chromatographed on 400 g silicagel with ethyl acetate.

9.2 g (91.5%) end-product was obtained as a colorless oil.

$R_f$ is 0.72 using a solvent system comprising ethyl acetate and methanol in a ratio of 10 to 1.

IR (film): 3350 (OH), 1740, 1725 (C=O), 965 cm$^{-1}$ (—CH=CH—).

$^1$H NMR (CDCl$_3$): 5.5–5.6 (m, 2H, —CH=CH—, J=15 Hz) 3.9–4.6 (4H, CH—O, 4H, COOCH$_2$—CH$_3$) 0.9 ppm (t, 3H, CH$_3$).

EXAMPLE 2

$3\alpha,\beta$-(1'-Ethoxycarbonyl-1'-cyanomethyl)-$6\beta$-(3S-hydroxy-oct-1E-enyl)-$7\alpha$-hydroxy-2-oxabicyclo[3.3.0]octane (compound of formula (I), wherein W is cyano, Y is ethoxycarbonyl, A, B, $R^2$, $R^4$, $R^5$ and $R^6$ are as defined in example 1)

2.7 g (10 mmoles) $3\alpha,\beta$-hydroxy-$6\beta$-(3S-hydroxy-oct-1E-enyl)-$7\alpha$-hydroxy-2-oxabicyclo[3.3.0]octane and 2.26 g (20 mmoles) cyanoacetic acid ethylester were dissolved in 20 ml water-free benzene, and 1 ml piperidinium acetate catalyst (prepared as described in example 1) was added to the solution. The reaction mixture was refluxed for two hours under a water separator, and was worked up as described in example 1. The 5 g crude product obtained by evaporation was chromatographed on 150 g silica gel with a 2:1 mixture of ethyl acetate and hexane.

3.4 g (92.5%) end-product was obtained as a colorless oil.

$R_f$ is 0.5 (ethyl acetate).

IR (film): 3350 (OH), 2290 (C≡N), 1750 cm$^{-1}$ (C=O).

$^1$H NMR (CDCl$_3$): δ5.5–5.6 (m, 2H, —CH=CH—), 4–4.6 ppm (4H, CH—O, 2H, COOCH$_2$—CH$_3$) 3.6 ppm (1H, NC—CH—COOEt).

EXAMPLE 3

$3\alpha,\beta$-(1'-Ethoxycarbonyl-2'-oxopropyl)-$6\beta$-(3S-hydroxy-oct-1E-enyl)-$7\alpha$-hydroxy-2-oxabicyclo[3.3.0]octane (compound of formula (I), wherein W is ethoxycarbonyl, Y is acetyl, A, B, $R^2$, $R^3$, $R^4$, $R^5$ and $R^6$ are as defined in example 1)

2.7 g (10 mmoles) 3α,β-hydroxy-6β-(3S-hydroxy-oct-1E-enyl)-7α-hydroxy-2-oxabicyclo[3.3.0]octane and 2.6 g (20 mmoles) acetoacetic acid were dissolved in 20 ml water-free benzene, and 0.8 ml piperidinium acetate catalyst (prepared as described in example 1) was added to the solution. The reaction mixture was refluxed for 3 hours under a water separator, and was worked up as described in example 1. The crude product obtained by evaporation was chromatographed on 150 g silica gel using ethyl acetate as an eluent.

3.25 g (85%) end-product was obtained as a colorless oil.

$R_f$ is 0.55 (ethyl acetate and methanol 10:1).
IR (film): 3350 (OH), 1740, 1720 cm$^{-1}$ (C=O).
$^1$H NMR (CDCl$_3$): δ5.5–5.6 (m, 2H, —CH=CH—). 4–4.6 (4H, CH—O, 2H, COOCH$_2$—CH$_3$) 2.1 ppm (s, 3H, O=C—CH$_3$).

EXAMPLE 4

3α,β-1',1'-Bis(ethoxycarbonyl)-methyl-6β-(3S-hydroxy-oct-1E-enyl)-7α-hydroxy-2-oxabicyclo[3.3.0]octane (compound of formula (I), wherein both W and Y are ethoxycarbonyl groups, A, B, $R^2$, $R^3$, $R^4$, $R^5$ and $R^6$ are as defined in example 1)

2.7 g (10 mmoles) 3α,β-hydroxy-6β-(3S-hydroxy-oct-1E-enyl)-7α-hydroxy-2-oxabicyclo[3.3.0]octane was dissolved in 8 g (50 mmoles) malonic acid diethylester under gentle heating and the colorless solution was cooled to room temperature. To the cool solution there was added 11 ml (11 mmoles) piperidine and the reaction mixture was allowed to stand at room temperature for 24 hours. The reaction was followed by thin layer chromatography. When the reaction completed the mixture was chromatographed on 300 g silica gel with ethyl acetate. The fractions containing the product were combined and the solvent was distilled off.

3.3 g (80%) end-product was obtained as a colorless oil.

$R_f$ is 0.57 (ethyl acetate).
IR (film): 3300 (OH), 1740–1750 cm$^{-1}$ (C=O).
NMR (CDCl$_3$): 5.5–5.6 (m, 2H, —CH=CH—) 4–4.6 ppm (4H, CH—O, 4H, COOCH$_2$).

EXAMPLE 5

3α,β-(1'-Acetyl-2'-oxopropyl)-6β-(3S-hydroxy-oct-1E-enyl)-7α-hydroxy-2-oxabicyclo[3.3.0]octane (compound of formula (I), wherein both W and Y are acetyl groups, A, B, $R^2$, $R^3$, $R^4$, $R^5$ and $R^6$ are as defined in example 1)

270 mg (1 mmole) 3α,β-hydroxy-6β-(3S-hydroxy-oct-1E-enyl)-7α-hydroxy-2-oxabicyclo[3.3.0]octane was dissolved in 2 g (20 mmoles) acetyl acetone under gentle heating. The solution was cooled to room temperature and 0.11 ml (1.1 mmoles) piperidine was added thereto. The reaction mixture was stirred for ten hours at room temperature, and the reaction mixture was chromatographed as obtained on 40 g silica gel with ethyl acetate. The fractions containing the reaction product were combined and the solvent was distilled off.

282 mg (80%) end-product was obtained as a colorless oil.

$R_f$ is 0.7 (ethyl acetate and methanol 10:1).
$^1$H NMR (CDCl$_3$): δ5.5–5.6 (m, 2H, —CH=CH—) 4–1.6 ppm (4H, CH—O) 2.2–2.3 ppm (6H, ss, O=C—CH$_3$).

EXAMPLE 6

3α,β-Nitromethyl-6β-(3S-hydroxy-oct-1E-enyl)-7α-hydroxy-2-oxabicyclo[3.3.0]octane 2.0 g (7.4 mmoles) 3α,β-hydroxy-6β-(3S-hydroxy-oct-1E-enyl)-7α-hydroxy-2-oxabicyclo[3.3.0]octane was dissolved in 20 ml nitromethane, 0.5 ml (5.1 mmoles) piperidine was added thereto and the reaction mixture was stirred at room temperature for twelve hours. The mixture was diluted with 100 ml ethyl acetate, and the organic solution was washed successively with 2×30 ml sodium bisulfate solution, 20 ml water and 20 ml saturated aqueous sodium chloride solution, then dried over sodium sulfate, filtered and the solvent was distilled off. The crude residue was chromatographed on 80 g silica gel with ethyl acetate. 2.0 g (86.3%) end-product was obtained as a pale yellow oil.

$R_f$ is 0.48 (ethyl acetate and acetone 10:1).
IR (film): 1560 cm$^{-1}$ (NO$_2$).
$^1$H NMR (CDCl$_3$): 5.4–5.5 (m, 2H, —CH=CH—) 4.5 ppm (m, 2H, CH$_2$—NO$_2$).

EXAMPLE 7

3α,β-Nitromethyl-6β-(3R-acetoxy-oct-1E-enyl)-7α-acetoxy-2-oxabicyclo[3.3.0]octane (compound of formula (I), wherein W is nitro, Y is hydrogen, $R^2$ is hydrogen having a steric position of α, $R^3$ is acetyl, A, B, $R^4$, $R^5$ and $R^6$ are as defined in example 1)

168 mg (0.47 mmoles) 3α,β-hydroxy-6β-(3S-hydroxy-oct-1E-enyl)-7α-hydroxy-2-oxabicyclo[3.3.0]octane was dissolved in 1.7 ml nitromethane and 50 μl (0.5 mmoles) piperidine was added thereto. The reaction mixture was stirred at room temperature for ten hours, then diluted with 20 ml ethyl acetate. The organic layer was washed successively with 5 ml sodium bisulfate solution, 5 ml water and 5 ml saturated aqueous sodium chloride solution, dried over sodium sulfate and the solvent was distilled off. The crude residue was chromatographed on 15 g silica gel with a 2:1 mixture of hexane and ethyl acetate.

160 mg (90%) end-product was obtained as a colorless oil.

$R_f$ is 0.27 (hexane and ethyl acetate 2:1).
IR (film): 1560 (NO$_2$), 1740 cm$^{-1}$ (C=O).

EXAMPLE 8

5-Nitro-PGI$_1$-methylester (compound of formula (I), W is nitro, Y is a group of formula Z=C—X—Q, Z means two hydrogens, X is —CH$_2$— —CH$_2$—, Q is methoxycarbonyl, the further substituents are as defined in example 1)

270 mg (1 mmole) 3α,β-hydroxy-6β-(3S-hydroxy-oct-1E-enyl)-7α-hydroxy-2-oxabicyclo[3.3.0]octane was dissolved in 2.7 ml (17 mmoles) 5-nitrovaleric acid methylester (compound of formula (III), wherein W is nitro, Y is

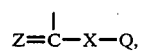

Z means two hydrogens, X is —CH$_2$—CH$_2$— and Q is methoxycarbonyl and 0.2 ml (2 mmoles) piperidine was added thereto. The reaction mixture was stirred for 72 hours at 60° C., then diluted with 40 ml ethyl acetate, and washed successively with 2×10 ml saturated aqueous sodium bisulfate solution, 10 ml water and 10 ml saturated aqueous saline solution, dried over sodium sulfate and the solvent was distilled off. The crude product obtained by evaporation was chromatographed on 40 g silica gel with ethyl acetate.

358 mg (86.2%) end-product was obtained as a colorless oil.

$R_f$ is 0.41 (ethyl acetate and acetone 10:1).

IR (film): 1560 ($NO_2$), 1740 $cm^{-1}$ (C—O).

$^1$H NMR ($CDCl_3$): $\delta$5.5–5.6 (m, 2H, —CH=CH—), 3.67 (s. 3H, $COOCH_3$), 3.6–4.6 (4H, CH—O, 1H, CH—$NO_2$).

EXAMPLE 9

5-Phenylsulfenyl-4-oxo-$PGI_1$-methylester (compound of formula (I), wherein W is $C_6H_5$—S—, the other substituents are as defined in example 1)

A mixture of 920 mg (3.4 mmoles) 3α,β-hydroxy-6β-(3S-hydroxy-oct-1E-enyl)-7α-hydroxy-2-oxabicyclo[3.3.0]-octane 1.64 g (6.88 mmoles) 5-phenylsulfenyl-4-oxo-valeric acid methylester, 5 ml benzene and 7 ml 0.5M piperidinium acetate benzene solution was boiled for 60 hours under a water separator. The reaction was followed by thin layer chromatography, and to the obtained mixture there was added 100 ml ethyl acetate, washed with 2×10 ml water, then with 10 ml saturated aqueous sodium chloride solution, dried over magnesium sulfate and the solvent was distilled off. The crude product was chromatographed on 30 g silica gel under 1.5 bar overpressure using ethyl acetate as eluent.

1.4 g (84%) end-product was obtained as a colorless oil.

$R_f$ is 0.46 using a 1:1 mixture of ethyl acetate and acetone as eluent.

IR (film): 1750, 1710 $cm^{-1}$ (C=O).

$^1$H NMR ($CDCl_3$): $\delta$7.4–7.6 (3H, m, aromatic), 7.0–7.2 (2H, m, aromatic), 5.6–5.7 (2H, m, —CH=CH—), 3.4–4.6 (7H, 2H replaceable by $D_2O$), (3.45 ppm (3H, s, $COOCH_3$).

EXAMPLE 10

5-p-Tolylsulfonyl-4-oxo-$PGI_1$-methylester (compound of formula (I), wherein W is p-tolylsulfonyl, the other substituents are as defined in example 1)

To a suspension of 500 m (1.85 mmoles) 3α,β-hydroxy-6β-(3S-hydroxy-oct-1E-enyl)-7α-hydroxy-2-oxabicyclo-[3.3.0]octane with 20 ml benzene there was added 1.31 g (4.88 moles) 5-p-tolylsulfonyl-4-oxo-valeric acid methylester, then 1.5 ml 0.5M piperidinium acetate benzene solution, and the reaction mixture was boiled for 36 hours under a water separator, then diluted with 50 ml ethyl acetate, successively washed with 2×10 ml water and 10 ml saturated aqueos sodium chloride solution, dried over magnesium sulfate, and the solvent was distilled off. The crude product was chromatographed on 25 g silica gel under an overpressure of 1.5 bar, using ethyl acetate as an eluent.

886 mg (89.3%) end-product was obtained as a colorless oil.

$R_f$ is 0.48 in the 1:1 mixture of ethyl acetate and acetone.

IR (film): 1720, 1750 $cm^{-1}$ (C=O);

$^1$H NMR ($CDCl_3$): $\delta$7.1–7.4 (4H, aromatic), 3.5–4.5 (5H, m), 3.67 (3H, s, $COOCH_3$), 2.47 ppm (3H, s).

EXAMPLE 11

5-Phenylsulfenyl-16,16-dimethyl-4-oxo-$PGI_1$-methylester (compound of formula (I), wherein W is a $C_6H_5$—S— group, $R_4$ and $R_5$ are both methyl and the other substituents are as defined in example 1)

To a solution of 1.2 g (4 mmoles) 3α,β-hydroxy-6β-(3S-hydroxy-4,4-dimethyl-oct-1E-enyl)-7α-hydroxy-2-oxabicyclo[3.3.0]octane prepared with 20 ml toluene there were added 2.86 g (12 mmoles) 5-phenylsulfenyl-4-oxo-valeric acid methylester and 10 ml 0.5M benzene piperidinium acetate solution, and the reaction mixture was boiled under a water separator for 20 hours. The reaction mixture was diluted with 100 ml ethyl acetate, the solution was washed with 2×10 ml water, then with 10 ml saturated aqueous sodium chloride dried over magnesium sulfate, and the solvent was distilled off. The crude product was chromatographed on silica gel using ethyl acetate as an eluent.

1.66 g (80%) end-product was obtained in the form of a pale yellow oil.

$R_f$ is 0.52 in ethyl acetate.

IR (film): 1745, 1710 $cm^{-1}$ (C=O).

$^1$H NMR ($CDCl_3$): $\delta$7.4–7.6 (3H, m), 7.0–7.2 (2H, m), 5.5–5.6 (2H, m), 3.57 ppm (3H, s).

EXAMPLE 12

5-p-Tolylsulfonyl-4-oxo-$PGI_1$-methylester-11,15-diacetate (compound of formula (I), wherein W is a p-tolylsulfonyl group, $R^3$ is acetyl, Q is methoxycarbonyl, the other substituents are as defined in example 1)

To a solution of 1 g (1.86 mmoles) 5-p-tolylsulfonyl-4-oxo-$PGI_1$-methylester (compound of example 10) prepared with 30 ml benzene there were added 3 ml pyridine and 0.53 ml (5.6 mmoles) acetic anhydride. The reaction took place within 12 hours at room temperature. To the reaction mixture then there was added 20 ml water, the mixture was stirred for 10 minutes, 150 ml ether was added thereto and the organic phase was washed successively with 5 ml 5N hydrochloric acid, 20 ml 1N hydrochloric acid, 20 ml water, 20 ml saturated aqueous sodium bicarbonate solution, 2×20 ml water and finally 20 ml saturated aqueous sodium chloride solution. The residue was dried over magnesium sulfate, filtered, and the solvent was distilled off. Chromatographing the product on a short column using a 1:1 mixture of ethyl acetate and hexane as an eluent, there were obtained 1.02 g (88%) end-product as a colorless oil.

$R_f$ is 0.31 in a 1:1 mixture of hexane and ethyl acetate.

$^1$H NMR ($CDCl_3$): 5.52 (2H, m), 5.15 (1H, m), 4.0–4.9 (4H, m), 3.65 (3H, s), 1.9–2.05 ppm (3H, s, 3H, s).

EXAMPLE 13

5-Phenylsulfenyl-4-oxo-valeric acid methylester

To 100 ml of a 1M methanolic sodium thiophenolate solution there was added 22 g (0.1 mole) 5-bromo-4-oxo-valeric acid methylester during 40 minutes and the reaction mixture was stirred for two hours at room temperature. The methanol was distilled off in vacuo, to the residue there was added 200 ml ethyl acetate, and the mixture was washed successively with 30 water, 30 ml sodium bicarbonate solution, 30 ml saturated saline solution, then dried over magnesium sulfate, filtered, and the solvent was distilled off. The residue was chromatographed on a column using a 4:1 mixture of hexane and ethyl acetate as an eluent.

21.3 g (85%) end-product was obtained as a colorless oil.

Boiling point: 128°–130° C. (0.2 Hgmm).

$^1$H NMR (CDCl$_3$): 7.2 (5H, m), 3.68 (2H, s), 3.56 (3H, s), 2.3–3.1 ppm (4H, m).

EXAMPLE 14

Disodium salt of 5-nitro-PGI$_2$ (compound of formula (I), wherein Y is a group of formula Z=C—X—Q, Z means two hydrogens, X is a —CH$_2$—CH$_2$— group, Q is —COONa, the other substituents are as defined in example 1)

116.15 mg (0.28 moles) 5-nitro-PGI$_1$-methylester (compound of example 8) was dissolved in 1 ml methanol, and 0.45 ml (1.12 mmoles) 2.5N sodium methoxide was added thereto. The reaction mixture was stirred at room temperature for 2 hours, then 10 μl (0.56 mmoles) water was added to the solution and it was stirred for twelve hours at room temperature. To the reaction mixture there was added 10 ml acetonitrile in small portions, the precipitated yellow crystalline material was filtered and dried at room temperature.

120 mg end-product was obtained in form of yellow-brownish crystals.

Melting point: above 200° C. (decomposes).

IR (KCl): 3450 cm$^{-1}$ (OH); 1580, 1430 cm$^{-1}$ (COO$^-$); 965 cm$^{-1}$ (—CH=CH—).

$^1$H NMR (D$_2$O): δ5.6 ppm (2H, —CH=CH—), 3.5–5 ppm (4H,

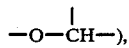

0.9 ppm (3H, —CH$_3$), 1–3 ppm (20H—).

EXAMPLE 15

13,14-Didehydro-5-nitro-PGI$_1$-methylester (compound of formula (I), wherein A is ethinylene, the other substituents are as defined in example 1)

268 mg (1 mmole) 3α,β-hydroxy-6β-(3S-hydroxy-oct-1E-enyl)-7α-hydroxy-2-oxabicyclo[3.3.0]octane was dissolved in 5 ml benzene, and 85 mg (1 mmole) piperidine, 10 mg (0.17 mmoles) acetic acid and 1.61 g (10 mmoles) 5-nitro-valeric acid methylester were added thereto. The reaction mixture was stirred for 48 hours at 60° C., then the process of example 8 was followed. The crude product was chromatographed on 40 g silica gel using a 2:1 mixture of ethyl acetate and hexane as an eluent.

309 mg (75%) end-product was obtained as a colorless oil.

R$_f$ is 0.54 in ethyl acetate.

IR (film): 1735 (C=O), 1560 cm$^{-1}$ (NO$_2$).

$^1$H NMR (CDCl$_3$): 4–4.6 (m, 5H, —CH—O—,

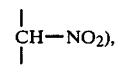

3.68 (s, 3H, COOCH$_3$).

EXAMPLE 16

15-Epi-5-nitro-PGI$_1$-benzylester (compound of formula (I), wherein Q is benzyloxycarbonyl, R$^2$ is hydrogen having a steric position of α, the other substituents are as defined in example 8)

2.7 g 3α,β-hydroxy-6β-(3R-hydroxy-oct-1E-enyl)-7α-hydroxy-2-oxabicyclo[3.3.0]octane was dissolved in 40 ml benzene, to the solution there was added 850 mg (10 mmoles) piperidine, 120 mg (2 mmoles) acetic acid and 11.2 g (50 mmoles) 5-nitro-valeric acid benzylester; further the process of example 8 was followed.

The crude product was chromatographed on 300 g silica gel using a 4:1 mixture of ethyl acetate and hexane as an eluent.

3.47 g (72%) end-product was obtained as a colorless oil.

R$_f$ is 0.28 in ethyl acetate.

IR (film): 1745 (C=O), 1560 cm$^{-1}$ (NO$_2$).

$^1$H NMR (CDCl$_3$): 7.4 (s, 5H, aromatic), 5.56 (m, 2H, —CH=CH), 5.15 (s, 2H, CO$_2$–CH$_2$), 3.7–4.6 (m, 5H).

EXAMPLE 17

16-Phenoxy-17,18,19,20-tetranor-5-nitro-PGI$_1$-methylester (compound of formula (I), wherein B is oxygen, R$^6$ is phenyl, the other substituents are as defined in example 9)

610 g (2 mmoles) 3α,β-hydroxy-6β-(1S-hydroxy-4-phenoxy)-but-1E-enyl)-7α-hydroxy-2-oxabicyclo[3.3.0]octane was dissolved in 10 ml benzene, and there were added 170 mg (2 mmoles) piperidine, 20 mg (0.34 mmoles) acetic acid and 3.2 g (20 mmoles) 5-nitro-valeric acid methylester to the mixture. The reaction mixture was stirred for 48 hours at 60° C., then the process of example 8 was followed. The crude product was chromatographed on 70 g silica gel using a 4:1 mixture of ethyl acetate and hexane as an eluent.

718 mg (80%) end-product was obtained as a colorless oil.

R$_f$ is 0.47 in a 10:1 mixture of ethyl acetate and acetone.

$^1$H NMR (CDCl$_3$): 7.4–7.1 (m, 5H, aromatic), 5.5–5.6 (m, 2H, —CH=CH), 3.7–4.8 (m, 7H), 3.68 (s, 3H, COOCH$_3$).

EXAMPLE 18

2-Decarboxy-2-hydroxymethyl-20-ethyl-5-nitro-PGI$_1$ (compound of formula (I), wherein Q is hydroxymethyl, R$^6$ is pentyl, the other substituents are as defined in example 9)

300 mg (1 mmole) 3α,β-hydroxy-6β-(3S-hydroxy-dec-1E-enyl)-7α-hydroxy-2-oxabicyclo[3.3.0]octane was dissolved in 5 ml benzene, and there were added 85 mg (1 mmole) piperidine, 10 mg (0.17 mmoles) acetic acid and 1.33 g (10 mmoles) 5-nitropentanol. The reaction mixture was stirred for 48 hours at 60° C., then the process of example 8 was followed. The crude product was chromatographed using a 10:1 mixture of ethyl acetate and acetone as an eluent.

318 mg (82%) end-product was obtained as a colorless oil.

R$_f$ is 0.45 in a 3:1 mixture of ethyl acetate and acetone.

IR (film): 3450 (OH), 1560 cm$^{-1}$ (NO$_2$).

$^1$H NMR (CDCl$_3$): 5.5–5.6 (m, 2H, —CH=CH), 3.7–4.8 (m, 7H), 0.91 (t, 3H, CH$_3$).

EXAMPLE 19

5-Nitro-PGI$_1$ sodium salt 978 mg (2.37 mmoles) 5-nitro-PGI$_1$-methylester was dissolved in a mixture of 7.1 ml (7.1 mmoles) 1N sodium hydroxide and 7 ml methanol, and the reaction mixture was stirred at room temperature for 24 hours. The methanol was distilled off in vacuo, to the residual aqueous solution there was added 20 ml acetonitrile, the precipitated product was filtered, washed with ether and dried in vacuo on calcium chloride.

1.05 g (100%) end-product was obtained in form of white crystals.

R$_f$ is 0.26 in a 20:10:1 mixture of benzene, dioxane and a acetic acid.

IR (KBr): 3450, 1500, 1440, 1330, 1170, 1050, 890, 830 cm$^{-1}$.

$^1$H NMR (DMSO-d$_6$): 5.5 (m, 2H, —CH=CH), 3.9–4.8 (m, 4H, —O—CH).

EXAMPLE 20

13,14-Didehydro-5-nitro-PGI$_1$ sodium salt 88 mg (0.214 mmoles) 13,14 didehydro-5-nitro-PGI$_1$-methylester was dissolved in 0.7 ml methanol, and 0.64 ml (0.64 mmoles) 1N sodium hydroxide solution was added thereto. Further the process of example 19 was followed.

95 mg (100%) end-product was obtained in form of white crystals.

R$_f$ is 0.38 in a 20:10:1 mixture of benzene, dioxane and acetic acid.

IR (KBr): 3450, 2250, 1435, 1320, 1145, 900 cm$^{-1}$.
$^1$H NMR (DMSO-d$_6$): 3.7–4.8 (m, 4H), 0.93 (t, 3H, —CH$_3$).

Following the process described in the above examples and starting from the corresponding compounds of formulae (II) or (III) the compounds of formula (I) listed hereinbelow were synthesized:

5-Phenylsulfenyl-13,14-didehydro-4-oxo-PGI$_1$-methylester (W=C$_6$H$_5$—S—)
R$_f$=0.56 (ethyl acetate-acetone 1:1);
5-Phenylsulfenyl-16-phenoxy-17,18,19,20-tetranor-4-oxo-PGI$_1$-methylester (W=C$_6$H$_5$—S—)
R$_f$=0.53 (ethyl acetate-acetone 1:1);
5-Phenylsulfenyl-16-(m-trifluormethylphenoxy)-17,18,19,20-tetranor-4-oxo-PGI$_1$-methylester (W=C$_6$H$_5$—S—)
R$_f$=0.4 (ethyl acetate-acetone 3:1);
5-Phenylsulfenyl-16-(m-chlorophenoxy)-17,18,19,20-tetranor-4-oxo-PGI$_1$-methylester (W=C$_6$H$_5$—S—)
R$_f$=0.29 (ethyl acetate);
5-Phenylsulfenyl-13,14-didehydro-20-ethyl-4-oxo-PGI$_1$-methylester (W=C$_6$H$_5$—S—)
R$_f$=0.58 (ethyl acetate-acetone 1:1);
2.5-Bis(phenylsulfenyl)-4-oxo-PGI$_1$-methylester (W=C$_6$H$_5$—S— and

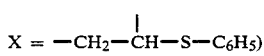

R$_f$=0.4 (ethyl acetate-acetone 1:1);
2,5-Bis(phenylsulfenyl)-13,14-didehydro-4-oxo-PGI$_1$-methylester (W=C$_6$H$_5$—S— and

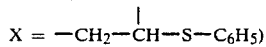

R$_f$=0.49 (ethyl acetate-acetone 1:1); and the salts and acids thereof obtained by hydrolysis;
16-(m-chlorophenoxy)-17,18,19,20-tetranor-5-nitro-PGI$_1$-methylester
R$_f$=0.5 (ethyl acetate);
16-(m-trifluoromethylphenoxy)-17,18,19,20-tetranor-5-nitro-PGI$_1$-methylester
R$_f$=0.54 (acetone-hexane 1:1);
2-phenylsulfenyl-5-nitro-PGI$_1$-methylester

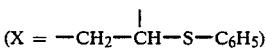

R$_f$=0.48 (ethyl acetate-acetone 10:1);
2-phenylsulfenyl-13,14-didehydro-5-nitro-PGI$_1$-methylester

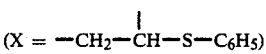

R$_f$=0.55 (ethyl acetate-acetone 10:1);
2-phenylsulfenyl-13,14-didehydro-20-ethyl-5-nitro-PGI$_1$-methylester

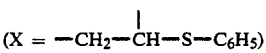

R$_f$=0.41 (ethyl acetate);
2-phenylsulfenyl-16-phenoxy-17,18,19,20-tetranor-5-nitro-PGI$_1$-methylester

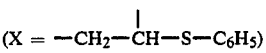

R$_f$=0.40 (ethyl acetate);
2-phenylsulfenyl-16-(m-chlorophenoxy)-17,18,19,20-tetranor-5-nitro-PGI$_1$-methylester

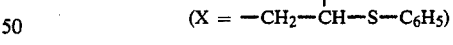

R$_f$=0.39 (ethyl acetate-acetone 4:1);
2-phenylsulfenyl-16-(m-trifluoromethylphenoxy)-17,18,19,20-tetranor-5-nitro-PGI$_1$-methylester

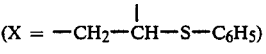

R$_f$=0.38 (ethyl acetate);
5-nitro-$\Delta^2$-PGI$_1$-methylester (X=—CH=CH—)
R$_f$=0.33 (ethyl acetate);
5-nitro-13,14-didehydro-$\Delta^2$-PGI$_1$-methylester (X=—CH=CH—)
R$_f$=0.39 (ethyl acetate);
5-nitro-13,14-didehydro-20-ethyl-$\Delta^2$-PGI$_1$-methylester (X=—CH=CH—)
R$_f$=0.42 (ethyl acetate);

5-nitro-15-epi-$\Delta^2$-PGI$_1$-methylester (X=—CH=CH—)
R$_f$=0.40 (ethyl acetate-acetone 3:1);
16-(m-chlorophenoxy)-17,18,19,20-tetranor-5-nitro-$\Delta^2$-PGI$_1$-methylester (X=—CH=CH—)
R$_f$=0.33 (ethyl acetate-acetone 4:1);
16-(m-trifluoromethylphenoxy)-17,18,19,20-tetranor-5-nitro-$\Delta^2$-PGI$_1$-methylester (X=—CH=CH—)
R$_f$=0.36 (ethyl acetate).

The R$_f$ values were determined on Merck Kieselgel 60 F$_{254}$ layers.

It is claimed:

1. A process for the preparation of a racemic or optically active compound of the formula I

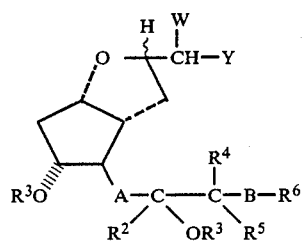

or a pharmaceutically acceptable salt thereof, wherein W is —COOR$^1$, —CN, —NO$_2$, C$_1$-C$_4$ alkanoyl, C$_1$-C$_4$ alkyl-sulfenyl, phenylsulfenyl, phenylsulfenyl where the phenyl is substituted by halogen, phenyl, C$_1$ to C$_4$ alkyl, or halo-C$_1$-C$_4$ alkyl, C$_1$-C$_4$ alkyl-sulfonyl, phenyl-sulfonyl, phenyl-sulfonyl where the phenyl is substituted by halogen, phenyl, C$_1$ to C$_4$ alkyl, or halo—C$_1$-C$_4$ alkyl, or W is phenyl-selenyl;

R$^1$ is hydrogen, C$_1$-C$_6$ straight or branched chain alkyl, C$_3$-C$_{10}$ cycloalkyl, phenyl—C$_1$-C$_4$ alkyl, or phenyl; Y is —COOR$^1$, —COR$^1$, —CN, or

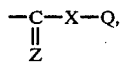

or when W is nitro, Y is also hydrogen;
Z is oxygen or when W is nitro Z represents two hydrogens;
X is —CH$_2$—CH$_2$—, —CH=CH—, —CH$_2$—C—(CH$_3$)$_2$—, —(CH$_3$)$_2$—C—CH$_2$—, phenyl-S—CH—CH$_2$—, —CH$_2$—CH—S—phenyl, or cyclopropylene;
Q is —COOM, —COOR$^1$, —CH$_2$OH, or COL$^1$, wherein M is pharmacologically active cation;
L$^1$ is —NH$_2$, —NHR$^1$ or NR$^1$R$^1$;
A is trans—CH=CH—, —C≡C—, or —CH$_2$—CH$_2$—;
R$^2$ is hydrogen having a steric position of $\alpha$ or $\beta$ or is methyl or ethyl;
R$^4$ and R$^5$ are independently hydrogen or C$_1$-C$_4$ alkyl;
R$^3$ is hydrogen or a protecting group which is C$_1$-C$_4$ alkanoyl, benzoyl, benzoyl substituted by halogen, phenyl, C$_1$-C$_4$ alkyl, or halo—C$_1$-C$_4$ alkyl, or is tri—C$_1$-C$_4$ alkyl-silyl;
R$^6$ is C$_1$ to C$_6$ straight or branched chain alkyl, phenyl or phenyl substituted by halogen, phenyl, C$_1$ to C$_4$ alkyl or halo—C$_1$ to C$_4$ alkyl; and B is methylene, oxygen or —NH—;
which comprises the step of:
reacting a compound of the formula II

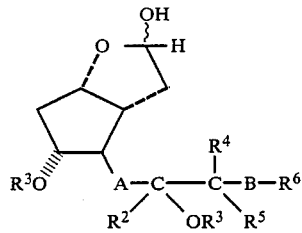

with a compound of the formula III

having an active methylene group, in the presence of a catalyst to obtain the desired product.

2. The process defined in claim 1 wherein the compound of the formula II is the solvent.

3. The process defined in claim 1 wherein an aromatic hydrocarbon, an aliphatic or atomatic halogenated-hydrocarbon or a dipolar-aprotic solvent is employed as a solvent.

4. The process defined in claim 1 wherein the catalyst is an organic amine, an organic amine salt, an organic acid, a sulfonic acid or a Lewis acid.

5. The process defined in claim 4 wherein the organic amine is piperidine and the organic amine salt is piperidinium acetate.

6. The process defined in claim 4 wherein the Lewis acid is boron trifluoride etherate, zinc (II) chloride or titanium (IV) chloride.

7. The process defined in claim 1 carried out at a temperature of 25° to 200° C.

8. The process defined in claim 1 further comprising the step of transforming the obtained compound of the formula I into another compound within the scope of formula I by hydrolysis, saponification, water or salt forming reactions, or by introducing a protecting group into the molecule.

9. A compound of the formula I

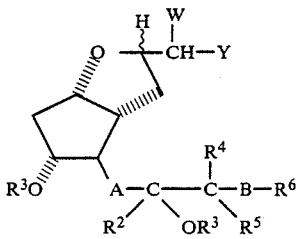

or a pharmaceutically acceptable salt thereof, wherein W is —NO$_2$, C$_1$-C$_4$ alkyl-sulfenyl, phenyl-sulfenyl, phenyl-sulfenyl where the phenyl is substituted by halogen, phenyl, C$_1$-C$_4$ alkyl, or halo—C$_1$-C$_4$ alkyl, C$_1$-C$_4$ alkyl-sulfonyl, phenyl-sulfonyl, phenyl-sulfonyl where the phenyl is substituted by halogen, phenyl, C$_1$-C$_4$ alkyl, or halo—C$_1$-C$_4$ alkyl, or W is phenyl-selenyl;

R$^1$ is hydrogen, C$_1$-C$_6$ straight or branched chain alkyl, C$_3$-C$_{10}$ cycloalkyl, phenyl—C$_1$-C$_4$ alkyl or phenyl;

Y is —COOR$^1$, —COR$^1$, —CN, or $$\underset{Z}{\overset{\parallel}{C}}-X-Q,$$

or when W is nitro, Y is also hydrogen;

Z is oxygen or when W is nitro Z represents two hydrogens;

X is —CH$_2$—CH$_2$, —CH=CH—, —CH$_2$—C—(CH$_3$)$_2$—, —(CH$_3$)$_2$—C—CH$_2$—, phenyl-S—CH—CH$_2$—, —CH$_2$—CH—S—phenyl, —or cyclopropylene;

Q is —COOM, —COOR$^1$, —CH$_2$OH, or —COL$^1$, wherein M is a pharmacologically active cation;

L$^1$ is —NH$_2$, —NHR$^1$ or —NR$^1$R$^1$;

A is trans—CH=CH—, —C≡C—, or —CH$_2$—CH$_2$—;

R$^2$ is hydrogen having a steric position of α or β or is methyl or ethyl;

R$^4$ and R$^5$ are independently hydrogen or C$_1$–C$_4$ alkyl;

R$^3$ is hydrogen or a protecting group which is C$_1$–C$_4$ alkanoyl, benzoyl, benzoyl substituted by halogen, phenyl, C$_1$–C$_4$ alkyl, or halo—C$_1$–C$_4$ alkyl, or is tri—C$_1$–C$_4$ alkyl-silyl;

R$^6$ is C$_1$–C$_6$ straight or branched chain alkyl, phenyl or phenyl substituted by halogen, phenyl, C$_1$–C$_4$ alkyl or halo—C$_1$–C$_4$alkyl; and B is methylene, oxygen, or —NH—.

10. 3α, β-nitromethyl-6β-(3S-hydroxy-oct-1E-enyl)-7-α-hydroxy-2-oxabicyclo(3,3,0) octane as defined in claim 9.

11. 3α,β-nitromethyl-6β-(3R-acetoxy-oct-1E-enyl)-7-α acetoxy-2-oxabicyclo(3,3,0)octane as defined in claim 9.

12. 5-nitro-PGI$_1$-methyl ester as defined in claim 9.

13. 5-phenylsulfenyl-4-oxo-PGI$_1$-methyl ester as defined in claim 9.

14. 5-p-tolylsulfonyl-4-oxo-PGI$_1$-methyl ester as defined in claim 9.

15. 5-phenylsulfenyl-16, 16-dimethyl-4-oxo-PGI$_1$-methyl ester as defined in claim 9.

16. 5-p-tolylsulfonyl-4-oxo-PGI$_1$-methyl ester-11, 15-diacetate as defined in claim 9.

17. The disodium salt of 5-nitro-PGI$_1$ as defined in claim 9.

18. 5-nitro-13,14-didehydro-PGI$_1$-methyl ester as defined in claim 9.

19. 15-epi-5-nitro-PGI$_1$-benzyl ester as defined in claim 9.

20. 16-phenoxy-17,18,19,20-tetranor-5-nitro-PGI$_1$-methyl ester as defined in claim 9.

21. 2-decarboxy-2-hydroxymethyl-5-nitro-20-ethyl PGI$_1$ as defined in claim 9.

22. The sodium salt of 5-nitro-PGI$_1$ as defined in claim 9.

23. The sodium salt of 5-nitro-13,14-didehydro-PGI$_1$ as defined in claim 9.

24. 5-phenylsulfenyl-13,14-didehydro-4-oxo-PGI$_1$-methyl ester as defined in claim 9.

25. 5-phenyl-sulfenyl-16-phenoxy-17,18,19,20-tetranor-4-oxo-PGI$_1$-methyl ester as defined in claim 9.

26. 5-phenyl-sulfenyl-16-(m-trifluoromethyl-phenoxy)-17,18,19,20-tetranor-4-oxo-PGI$_1$-methyl ester as defined in claim 9.

27. 5-phenyl-sulfenyl-16(m-chlorophenoxy)-17,18,19,20-tetranor-4-oxo-PGI$_1$-methyl ester as defined in claim 9.

28. 5-phenyl-sulfenyl-13,14-didehydro-20-ethyl-4-oxo-PGI$_1$-methyl ester as defined in claim 9.

29. 2,5-bis(phenylsulfenyl)-4-oxo-PGI$_1$-methyl ester as defined in claim 9.

30. 2,5-bis-(phenylsulfenyl)-13,14-didehydro-4-oxo-PGI$_1$-methyl ester as defined in claim 9.

31. 5-nitro-16-(m-trifluoromethylphenoxy)-17,18,19,20-tetranor-PGI$_1$-methyl ester as defined in claim 9.

32. 5-nitro-16-(m-chlorophenoxy)-17,18,19,20-tetranor-PGI$_1$-methyl ester as defined in claim 9.

33. 5-nitro-2-phenylsulfenyl-PGI$_1$-methyl ester as defined in claim 9.

34. 5-nitro-13,14-didehydro-2-phenylsulfenyl-PGI$_1$-methyl ester as defined in claim 9.

35. 5-nitro-13,14-didehydro-2-phenylsulfenyl-20-ethyl-PGI$_1$-methyl ester as defined in claim 9.

36. 5-nitro-2-phenylsulfenyl-16-phenoxy-17,18,19,20-tetranor-PGI$_1$-methyl ester as defined in claim 9.

37. 5-nitro-2-phenylsulfenyl-16-(m-chlorophenoxy)-17,18,19,20-tetranor-PGI$_1$-methyl ester as defined in claim 9.

38. 5-nitro-2-phenylsulfenyl-16-(m-trifluoromethylphenoxy)-17,18,19,20-tetranor-PGI$_1$-methyl ester as defined in claim 9.

39. 5-nitro-Δ$^2$-PGI$_1$-methyl ester as defined in claim 9.

40. 5-nitro-13,14-didehydro-Δ$^2$-PGI$_1$ methyl ester as defined in claim 9.

41. 5-nitro-13,14-didehydro-20-ethyl-Δ$^2$-PGI$_1$ methyl ester as defined in claim 9.

42. 5-nitro-15-epi-Δ$^2$-PGI$_1$ methyl ester as defined in claim 9.

43. 5-nitro-16-(m-chlorophenoxy)-Δ$^2$-17,18,19,20-tetranor-PGI$_1$ methyl ester as defined in claim 9.

44. 5-nitro-16-(m-trifluoromethylphenoxy)-Δ$^2$-17,18,19,20-tetranor-PGI$_1$ methyl ester as defined in claim 9.

45. A compound of the formula III

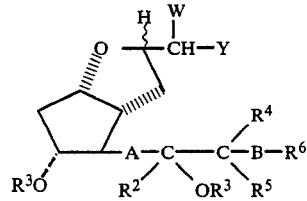

or a pharmaceutically acceptable salt thereof, wherein

W is —COOR$^1$;

Y is —COOR$^1$;

R$^1$ is hydrogen, straight or branched chain alkyl of 1 to 6 carbon atoms, C$_3$–C$_{10}$ cycloalkyl, phenyl—C$_1$–C$_4$ alkyl or phenyl;

A is trans—CH=CH—, —C≡C—, or —CH$_2$—CH$_2$—;

R$^2$ is hydrogen having a steric position of α or β or is methyl or ethyl;

R$^4$ and R$^5$ are independently hydrogen or C$_1$–C$_4$ alkyl;

R³ is hydrogen or a protecting group which is C₁-C₄ alkanoyl, benzoyl, benzoyl substituted by halogen, phenyl, C₁-C₄ alkyl or halo—C₁-C₄ alkyl, or is tri—C₁-C₄ alkyl-silyl;

R⁶ is C₁-C₆ straight or branched chain alkyl, phenyl or phenyl substituted by halogen, phenyl, C₁-C₄ alkyl or halo—C₁-C₄ alkyl; and B is methylene, oxygen or —NH—.

46. 3α,β-(1'1'-bis(ethoxycarbonyl)-methyl)-6β-(3S-hydroxy-oct-1E-enyl)-7-α-hydroxy-2-oxabicyclo-(3,3,0)-octane as defined in claim 45.

47. A compound of the formula I

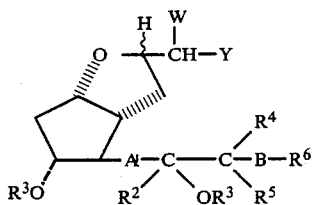

or a pharmaceutically acceptable salt thereof, wherein
W is —COOR¹, —CN —NO₂, C₁-C₄ alkanoyl, C₁-C₄ alkylsulfenyl, phenyl-sulfenyl, phenyl-sulfenyl where the phenyl is substituted by halogen, phenyl, C₁-C₄ alkyl, or halo—C₁-C₄ alkyl, C₁-C₄ alkyl-sulfonyl, phenyl-sulfonyl, phenyl-sulfonyl where the phenyl is substituted by halogen, phenyl, C₁-C₄ alkyl, or halo—C₁-C₄ alkyl, or W is phenyl-selenyl;

R¹ is hydrogen, C₁-C₆ straight or branched chain alkyl, C₃-C₁₀ cycloalkyl, phenyl—C₁-C₄ alkyl or phenyl;

Y is —CN or

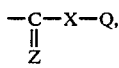

or when W is nitro, Y is also hydrogen;
Z is oxygen or where W is nitro Z represents two hydrogens;
X is —CH₂—CH₂—, —CH=CH—, —CH₂—C(CH₃)₂—, —(CH₃)₂—C—CH₂—, phenyl-S—CH—CH₂—, —CH₂—CH—S—phenyl, or cyclopropylene;
Q is —CH₂OH, or —COL¹, wherein L¹ is —NH₂, —NHR¹, or —NR¹R¹;
A is trans—CH=CH—, —C≡C—, or —CH₂—CH₂—;
R² is hydrogen having a steric position of α or β or is methyl or ethyl;
R⁴ and R⁵ are independently hydrogen or C₁-C₄ alkyl;
R³ is hydrogen or a protecting group which is C₁-C₄ alkanoyl, benzoyl, benzoyl substituted by halogen, phenyl, C₁-C₄ alkyl, or halo—C₁-C₄ alkyl, or is tri—C₁-C₄ alkyl-silyl;
R⁶ is C₁-C₆ straight or branched chain alkyl, phenyl or phenyl substituted by halogen, phenyl, C₁-C₄ alkyl or halo—C₁-C₄ alkyl; and B is methylene, oxygen or —NH—.

48. 3α,β-(1'-ethoxycarbonyl-1'-cyanomethyl)-6β-(3S-hydroxy-oct-1E-enyl)-7α-hydroxy-2-oxabicyclo(3,3,0)-octane as defined in claim 47.

49. A compound of the formula I

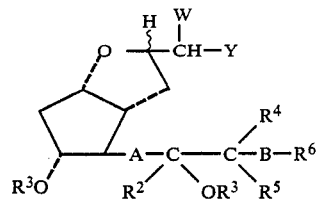

or a pharmaceutically acceptable salt thereof, wherein
W is C₁-C₄ alkanoyl;
Y is —COR¹;
R¹ is hydrogen, straight or branched chain alkyl of 1 to 6 carbon atoms, C₃-C₁₀ cycloalkyl, phenyl—C₁-C₄ alkyl or phenyl;
A is trans—CH=CH—, —C≡C—, or —CH₂—CH₂—;
R² is hydrogen having a steric position of α or β or methyl or ethyl;
R⁴ and R⁵ are independently hydrogen or C₁-C₄ alkyl;
R³ is hydrogen or a protecting group which is C₁-C₄ alkanoyl, benzoyl, benzyl substituted by halogen, phenyl, C₁-C₄ alkyl, or halo—C₁-C₄ alkyl, or is tri—C₁-C₄ alkyl-silyl;
R⁶ is C₁-C₆ straight or branched chain alkyl, phenyl or phenyl substituted by halogen, phenyl, C₁-C₄ alkyl or halo—C₁-C₄ alkyl; and
B is methylene, oxygen or —NH—.

50. 3α,β-(1'-acetyl-2'-oxopropyl)-6β-(3S-hydroxy-oct-1E-enyl)-7α hydroxy-2-oxabicyclo(3,3,0)octane as defined in claim 49.

51. A compound of the formula I

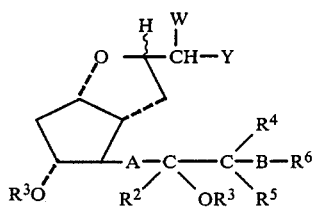

or a pharmaceutically acceptable salt thereof, wherein
W is —CN, —NO₂, C₁-C₄ alkanoyl, C₁-C₄ alkylsulfenyl, phenyl-sulfenyl, phenyl-sulfenyl where the phenyl is substituted by halogen, phenyl, C₁-C₄ alkyl, or halo—C₁-C₄ alkyl, C₁-C₄ alkyl-sulfonyl, phenyl-sulfonyl, phenyl-sulfonyl where the phenyl is substituted by halogen, phenyl, C₁-C₄ alkyl, or halo—C₁-C₄ alkyl, or W₁ is phenyl-selenyl;
R¹ is hydrogen, C₁-C₆ straight or branched chain alkyl, C₃-C₁₀ cycloalkyl, phenyl—C₁-C₄ alkyl or phenyl;
Y is —CN or

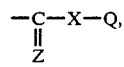

or when W is nitro, Y is also hydrogen;

Z is oxygen or where W is nitro Z represents two hydrogens;

X is —CH$_2$—CH$_2$—, —CH=CH—, —CH$_2$—C(CH$_3$)$_2$—, —(CH$_3$)$_2$—C—CH$_2$—, $$\text{phenyl-S—CH—CH}_2\text{—}, \quad \text{—CH}_2\text{—CH—S—phenyl},$$

or cyclopropylene;

Q is —COOM, —COOR$^1$, —CH$_2$OH, or —COL$^1$, wherein M is a pharmacologically active cation;

L$^1$ is —NH$_2$, —NHR$^1$, or —NR$^1$R$^1$;

A is trans—CH=CH—, —C≡C—, or —CH$_2$—CH$_2$—;

R$^2$ is hydrogen having a steric position of α or β or is methyl or ethyl;

R$^4$ and R$^5$ are independently hydrogen or C$_1$-C$_4$ alkyl;

R$^3$ is hydrogen or a protecting group which is C$_1$-C$_4$ alkanoyl, benzoyl, benzoyl substituted by halogen, phenyl, C$_1$-C$_4$ alkyl, or halo—C$_1$-C$_4$ alkyl, or is tri—C$_1$-C$_4$ alkyl-silyl;

R$^6$ is C$_1$-C$_6$ straight or branched chain alkyl, phenyl or phenyl substituted by halogen, phenyl, C$_1$-C$_4$ alkyl or halo—C$_1$-C$_4$ alkyl; and B is methylene, oxygen or —NH—.

52. A vasodilatory, blood platelet antiaggregating, or bronchodlating method of treatment which comprises the step of administering to a subject in need thereof an effective amount of a compound defined in claim 9 or a pharmaceutically acceptable salt thereof.

53. A vasodilatory, blood platelet antiaggregating, or bronchodilating method of treatment which comprises the step of administering to a subject in need thereof an effective amount of a compound defined in claim 45 or a pharmaceutically acceptable salt thereof.

54. A vasodilatory, blood platelet antiaggregating, or bronchodilating method of treatment which comprises the step of administering to a subject in need thereof an effective amount of a compound defined in claim 47 or a pharmaceutically acceptable salt thereof.

55. A vasodilatory, blood platelet antiaggregating, or bronchodilating method of treatment which comprises the step of administering to a subject in need thereof an effective amount of the compound defined in claim 49 or a pharmaceutically acceptable salt thereof.

56. A vasodilatory, blood platelet antiaggregating, or bronchodilating method of treatment which comprises the step of administering an effective amount of a compound defined in claim 51 or a pharmaceutically acceptable salt thereof.

* * * * *